United States Patent [19]

Döme et al.

[11] Patent Number: 4,897,548

[45] Date of Patent: Jan. 30, 1990

[54] APPARATUS FOR THE MULTIPLE ANALYSIS OF GASES

[75] Inventors: Peter Döme, Hombrechtikon; Heinz Wagner; Alfred Meier, both of Zurich, all of Switzerland

[73] Assignee: Tecan AG Analytische Instrumente, Hombrechtikon, Switzerland

[21] Appl. No.: 259,524

[22] Filed: Oct. 18, 1988

[30] Foreign Application Priority Data

Oct. 19, 1987 [CH] Switzerland ............... 04090/87-2

[51] Int. Cl.$^4$ ............... G01N 21/27; G01N 21/76
[52] U.S. Cl. ............... 250/343; 250/347 WGW; 250/361 C; 422/52; 422/83
[58] Field of Search ............... 422/52, 68, 83; 436/116, 135, 172; 250/343, 347, 373, 361 C, 368; 356/244, 246

[56] References Cited

U.S. PATENT DOCUMENTS

| | | | |
|---|---|---|---|
| 3,813,146 | 5/1974 | Burch et al. | 356/229 |
| 3,963,928 | 6/1976 | Zolner | 250/361 C |
| 4,207,469 | 6/1980 | Hopkins et al. | 250/343 |
| 4,467,203 | 8/1984 | Rappaport | 250/343 |
| 4,525,627 | 6/1985 | Krempl et al. | 250/343 |
| 4,775,637 | 10/1988 | Sutherland et al. | 436/172 |

FOREIGN PATENT DOCUMENTS 2016679 9/1979 United Kingdom .

Primary Examiner—David L. Lacey
Assistant Examiner—Gregory R. Muir
Attorney, Agent, or Firm—Walter C. Farley

[57] ABSTRACT

An apparatus for the multiple analysis of gases which can react with another gas to produce emission of light has at least two reaction chambers (1a, 1b), a single photodetector (3) and an optical redirection system (2) with a reflection surface movably mounted between the reaction chambers for sequentially and rapidly redirecting the light from the two reaction chambers onto the single photodetector for evaluation.

7 Claims, 1 Drawing Sheet

APPARATUS FOR THE MULTIPLE ANALYSIS OF GASES

The invention relates to apparatus for the multiple analysis of gases which can react with other gases in reactions accompanied by the emission of light, with at least two reaction chambers and one photodetector, and also to the utilization of such a device for chemiluminescence analysis, particularly for the analysis of $NO/NO_x$.

BACKGROUND OF THE INVENTION

For a large number of gas analysis situations, it is required to pursue several reactions simultaneously or at least substantially simultaneously, and to measure them with one and the same detector.

The hitherto known devices for such multiple analyses of gases all operate with an optical-fiber system. GB-A 2,016,679, e.g., discloses a chemiluminescence gas analyzer with two reaction chambers, in which light emitted from two reaction chambers is in each instance transmitted by means of a mechanical interrupt ("chopper") to one of the branches of a Y-shaped light-conductor which conducts the light to a single, central photodetector. In order to maintain the necessary level of quality, large-cross-section light conductors are necessary, which are extraordinarily expensive.

SUMMARY OF THE INVENTION

This invention is designed to provide relief in this regard. An object of the invention is the observation and/or measurement of several gas reactions occurring simultaneously in different reaction chambers, using one and the same photodetector, and without using any additional fiber optic light conductors.

The advantages achieved by the invention are essentially characterized in that, thanks to the inventive device, the reaction chambers can be designed with great freedom, both in terms of dimension and in terms of shape, together with optimum adaptation of the reaction volume to the active photodetector surface, so that small-surface, cheap photodetectors may be used, and the utilization of expensive light-conductors can be dispensed with.

Additional advantages include the following:

The optical reproduction or reflection system used in the device according to the invention has a small mass which need only be moved along very small distances; this permits rapid transfer from one reaction chamber to the other.

The sequence of the reactions to be measured in several reaction chambers, and also the measurement times, can be selected entirely as desired, so that maximum flexibility of measurement modes is provided.

It is easy to achieve the interposition of a "blind phase," in which entry of light is suppressed for the dark-current measurement of the detector, without a chopper being necessary.

Thanks to periodic deflection of the reaction light, the rapidly-movable optical reflection system permits the generation of an alternating signal at the photodetector.

For the investigation of periodically occurring test gases, (e.g., in internal combustion engines), a synchronized deflection mechanism can be incorporated by means of a phase-shifter for analysis of the time-reaction profile.

The simultaneous determination of a number of nitrogen compounds is facilitated by the fact that, e.g., three reactions may be measured substantially simultaneously; in this way, the utilization of two converters operating at different temperatures provides for the possibility of simultaneous determination of NO, $NO_2$, and $NH_3$.

For reaction chambers linked in series, chemiluminescence sequences with differing reaction times may be measured. This leads to the direct ascertainment of parasitic reaction of disruptive components, and permits the correction of the measurement signal to the sole relevant major component of the measurement gas.

The preferred utilization of the inventive device is chemiluminescence analysis, particularly the analysis of $NO/NO_x$. In chemiluminescence analysis, the light energy E liberated in the reaction equation $$NO + O_3 \rightarrow NO_2 + O_2 + E$$

can be utilized for the measurement of the NO concentration, since it is proportional to the NO concentration in the measurement gas, given an excess of $O_3$. This light emission can be measured by means of a sensitive light detector, e.g., a photo-multiplier tube (PMT), and transformed into a measurement signal by means of an electronic measuring device. The ozone required for the reaction is generated by means of an ozone generator. Chemiluminescence technology is considered the most reliable continuous measurement method for oxides of nitrogen. For the measurement of the $NO_2$ content, the gas mixture to be analyzed, which generally contains both NO and $NO_2$ ($NO_x$) is first passed through a so-called converter which reduces $NO_2$ to NO.

BRIEF DESCRIPTION OF THE DRAWING

An exemplary embodiment of the invention, which at the same time elucidates the functional principle, is represented in the drawing, and is explained in greater detail below, FIG. 1 showing a schematic diagram of an apparatus in accordance with the invention with two reaction chambers.

DESCRIPTION OF THE PREFERRED EMBODIMENT

Figure 1:
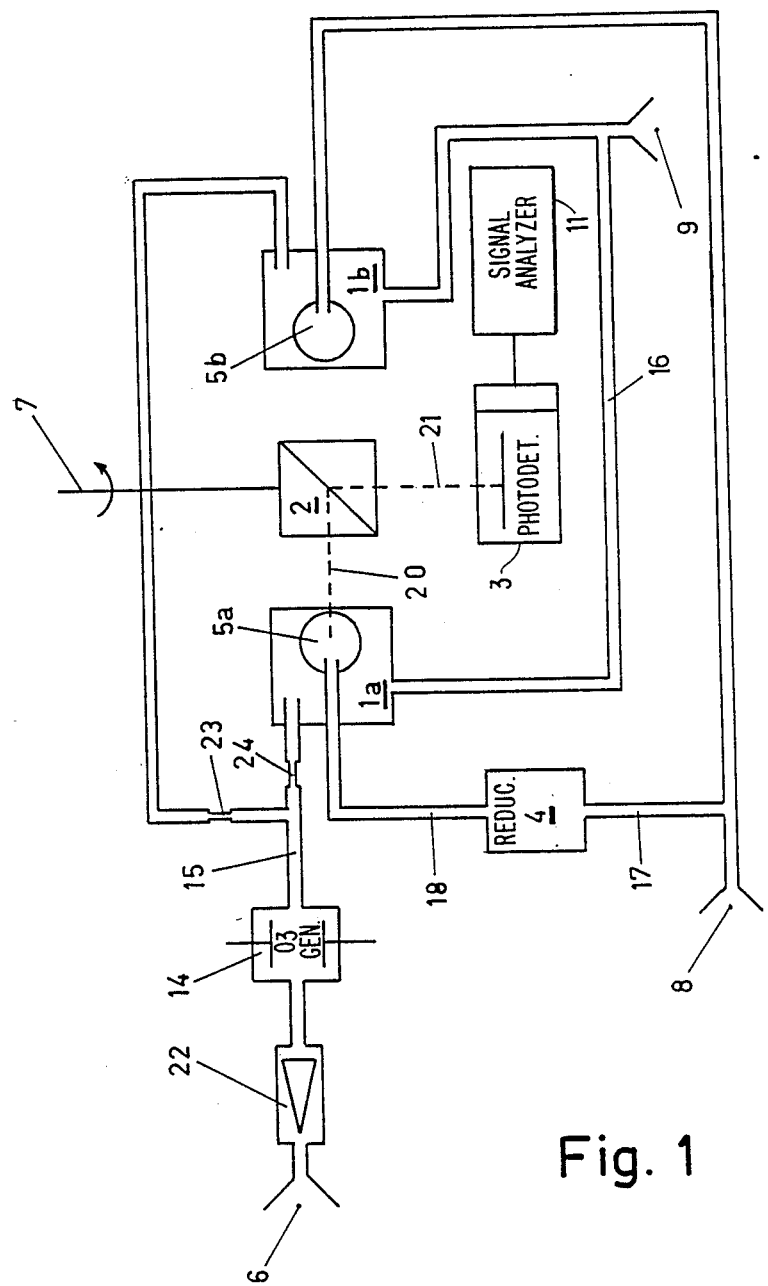

The embodiment shown in FIG. 1 is designed to measure $NO/NO_x$. It permits the simultaneous measurement of NO and $NO_2$ concentrations in a test gas which is introduced to the analyzer through the test-gas intake 8. This measurement occurs by substantially simultaneous measurement of the chemiluminescence in two reaction chambers 1a, 1b. In reaction chamber 1b, the NO portion of the gas to be measured reacts. In reaction chamber 1a, the NO proportional to the $NO_x$, i.e., the total oxide-of-nitrogen share of the test gas, e.g. also including the $NO_2$ concentration, reacts. In order to ascertain these, the test gas for the reaction chamber 1a is passed through a test-gas conduit 17 into a converter 4 which reduces $NO_2$ to NO, and leads the NO through conduit 18 to the reaction chamber 1a.

Air is then added through an air intake 6, which has a flow-through measuring device 22, to an ozone generator 14, in a controlled manner. The ozone gas thus created is then passed through gas conduit 15, which divides into conduits with capillaries 23 and 24, to the two reaction chambers 1a, 1b.

The gas reactions occurring in reaction chambers 1a, 1b cause corresponding chemiluminescences. In FIG. 1, the path 20 of the light exiting from the reaction chamber 1a is shown; it is deflected by the prism 2 at a right angle (light ray 21) to a photomultiplier tube 3. A redirection drive mechanism, not shown in the FIGURE, rotates the prism 2 back and forth in rapidly changing sequence about its axis 7, so that the light emissions from the reaction chambers 1a and 1b are reflected alternately by the prism 2 to photomultiplier tube 3.

The housing of the photomultiplier tube (not shown) may be cooled and thermostatically regulated by means of Peltier elements in order to reduce background noise and measuring signal fluctuation, particularly drift due to variations in signal amplification. An optical infrared filter (not shown) can be mounted between the reaction chambers 1a,1b and the photomultiplier tube 3. The light emission received by the photomultiplier 3 can be displayed through a signal analyzer 11.

The reaction gases are passed through the gas conduits 16 of the two reaction chambers 1a,1b, to exhaust 9.

If required, additional pressure-regulating valves, three-way magnetic valves, through-flow meters, vacuum pumps, activated carbon filters and capillaries (all not shown) can be built into the analysis circuit.

We claim:

1. An apparatus for the multiple analysis of gases which emit light when reacted with other gases, the apparatus comprising
   a plurality of chemiluminescence reaction chambers (1a, 1b) from each of which reaction chamber light is emitted when gases react therein;
   a single photodetector (3);
   an optical reflector (2) having a reflecting surface contained in a plane;
   means for mounting said optical reflector for rotational motion about an axis which forms an acute angle with the plane containing said reflecting surface; and
   drive means for moving said reflector in rapid sequence between a plurality of positions such that said light 2. An apparatus according to claim 1 wherein said optical reflector is a prism.

3. An apparatus according to claim 2 which further includes means (17, 18) for flowing a stream of test gas into a first one of said reaction chambers (1a) and a converter (4) for the reduction of $NO_2$ to NO positioned in said means for flowing, serially upstream of said first one of said reaction chambers (1a).

4. An apparatus according to claim 3 wherein said optical reflector is mounted between said reaction chambers (1a, 1b) on a line extending between the centers of said reaction chambers.

5. An apparatus according to claim 1 wherein said optical reflector is a mirror.

6. An apparatus according to claim 5 which further includes means (17,18) for flowing a stream of test gas into a first one of said reaction chambers (1a) and a converter (4) for the reduction of $NO_2$ to NO positioned in said means for flowing, serially upstream of one of said reaction chambers (1a).

7. An apparatus according to claim 6 wherein said optical reflector is mounted between said reaction chambers (1a, 1b) on a line extending between the centers of said reaction chambers.

* * * * *